United States Patent [19]

Johnson

[11] Patent Number: 4,558,138

[45] Date of Patent: Dec. 10, 1985

[54] CATALYTIC HYDROGENATION OF SULFOLENES

[75] Inventor: Marvin M. Johnson, Bartlesville, Okla.

[73] Assignee: Phillips Petroleum Company, Bartlesville, Okla.

[21] Appl. No.: 718,048

[22] Filed: Mar. 29, 1985

[51] Int. Cl.$^4$ .......................................... C07D 333/48
[52] U.S. Cl. ...................................................... 549/87
[58] Field of Search ......................................... 549/87

[56] References Cited

U.S. PATENT DOCUMENTS

| | | | |
|---|---|---|---|
| 3,152,144 | 10/1964 | Middlebrook | 260/332.1 |
| 3,417,103 | 12/1968 | Warner | 260/332.1 |
| 3,514,469 | 5/1970 | Phillips et al. | 260/332.1 |
| 3,622,598 | 11/1971 | Willis | 260/332.1 |
| 4,188,327 | 2/1980 | Kubicek | 549/87 |

FOREIGN PATENT DOCUMENTS

| | | | |
|---|---|---|---|
| 717071 | 8/1965 | Canada | 549/87 |
| 654464 | 6/1951 | United Kingdom | 549/87 |

OTHER PUBLICATIONS

"Comprehensive Inorganic Chemistry", vol. 2, by J. C. Bailar et al., 1973, Pergamon Press, pp. 882, 883.

*Primary Examiner*—Alan Siegel
*Attorney, Agent, or Firm*—French and Doescher

[57] ABSTRACT

A sulfolene compound, especially 3-sulfolene, containing dissolved sulfur dioxide as impurity is contacted with an oxidizing agent selected from the group of (a) peroxomonosulfuric acid, (b) peroxodisulfuric acid, (c) peroxomonosulfates and an acid having a pKa less than 4, and (d) peroxodisulfates and an acid having a pKa of less than 4, so as to remove at least a portion of dissolved $SO_2$. Preferred agents are $KHSO_5$ and $H_2SO_4$. The thus purified sulfolene compound, particularly 3-sulfolene, can be hydrogenated to a sulfolane compound over a suitable catalyst, e.g., Raney nickel.

19 Claims, No Drawings

CATALYTIC HYDROGENATION OF SULFOLENES

BACKGROUND OF THE INVENTION

This invention relates to a process for catalytically hydrogenating sulfolenes to sulfolanes. In another aspect, this invention relates to a process for hydrogenating sulfolenes to sulfolanes over a nickel catalyst. In a further aspect, this invention relates to pretreating sulfolenes so as to remove impurities, particularly $SO_2$, which interfere with the subsequent catalytic hydrogenation of sulfolenes.

The catalytic hydrogenation of sulfolenes to sulfolanes is well known. Generally a supported nickel catalyst is employed. Also the removal of sulfur dioxide and other impurities from sulfolenes by means of oxidizing agents has been disclosed, e.g., in U.S. Pat. Nos. 3,622,958; 3,514,469; 3,417,103 and 3,152,144. However, there is an ever present need to find still more effective methods of removing impurities from sulfolenes so as to speed up the subsequent hydrogenation of sulfolenes to sulfolanes and to reduce the amount of catalyst used.

SUMMARY OF THE INVENTION

It is an object of this invention to remove dissolved $SO_2$ and other impurities from a sulfolene. It is another object of this invention to remove $SO_2$ and other hydrogenation-retarding impurities from a sulfolene by treatment with an oxidizing agent. It is a further object to remove said impurities by said treatment prior to the hydrogenation of a sulfolene to a sulfolane over a nickel catalyst. Further objects and advantages will become apparent from the following disclosure and appended claims.

In accordance with this invention, a sulfolene compound containing dissolved $SO_2$ is contacted with at least one oxidizing agent selected from the group consisting of peroxomonosulfuric acid, peroxodisulfuric acid, peroxomonosulfates plus at least one acid having a pKa of less than 4, and peroxodisulfates plus an acid having a pKa of less than 4, under such conditions as to produce a sulfolene compound having a reduced level of dissolved $SO_2$. In one embodiment, an acid having a pKa of less than 4 and an alkali metal peroxomonosulfate is added to 3-sulfolene ($C_4H_6SO_2$) prior to its being catalytically hydrogenated to sulfolane ($C_4H_8SO_2$).

DETAILED DESCRIPTION OF THE INVENTION

The term "a sulfolene" (somtimes also referred to as "sulfolenes" and "sulfolene compounds") as employed herein is defined in U.S. Pat. No. 3,622,598, herein incorporated by reference. This term includes substituted and unsubstituted 3-sulfolenes and 2-sulfolenes. The preferred sulfolene compound employed in this invention is unsubstituted 3-sulfolene, which is commercially available and is produced by reaction of 1,3-butadiene and sulfur dioxide. The terms "sulfolane" or "sulfolane compounds" are also defined in U.S. Pat. No. 3,622,598.

The term pKa is defined as the negative logarithm of the ionization constrant Ka of an acid (pKa = $-_{10}$log Ka). The determination of the ionization constant Ka and its definition is explained in "Physical Chemistry", F. Daniels and R. Alberty, Second Edition, 1961, John Wiley and Sons, Inc., pages 364, 365, 428–430, herein incorporated by reference. Thus an acid having a pKa of less than 4 has an ionization constant $(H^+)(A^-)/(HA)$ of greater than $10^{-4}$. If a polyprotic acid is employed, Ka refers to the dissociation of the first hydrogen. It is understood that the term acid includes acid salts such as $KHSO_4$, wherein the $HSO_4^-$ ion can further ionize to $H^+$ and $SO_4^{2-}$.

In the process of this invention, at least one sulfolene compound, preferably 3-sulfolene ($C_4H_6SO_2$), is treated with at least one oxidizing agent selected from the group consisting of (a) peroxomonosulfuric acid ($H_2SO_5$), (b) peroxodisulfuric acid ($H_2S_2O_8$), (c) peroxomonosulfates (i.e., compounds containing the $HSO_5^-$ or $SO_5^{2-}$ ion) and at least one acid having a pKa value of less than 4, and (d) peroxodisulfates (e.g., compounds containing the $HS_2O_8^-$ or $S_2O_8^{2-}$ ion) and at least one acid having a pKa value of less than 4, so as to reduce the level of sulfur dioxide dissolved in said sulfolene compound. It is understood that the acid in (c) and (d) can be (a) or (b). The treatment of a sulfolene compound with said oxidizing agent results in the oxidation of dissolved $SO_2$ to compounds having a higher oxidation state of sulfur. It is believed that the reduced concentration of $SO_2$ in the sulfolene results in an enhanced rate of catalytic hydrogenation to sulfolane.

Non-limiting examples of peroxomonosulfates are $LiHSO_5$, $Li_2SO_5$, $NaHSO_5$, $Na_2SO_5$, $KHSO_5$, $K_2SO_5$, $NH_4HSO_5$, $(NH_4)_2SO_5$, $Mg(HSO_5)_2$, $MgSO_5$, $Ca(HSO_5)_2$, $CaSO_5$, $Ba(HSO_5)_2$, $BaSO_5$, $Zn(HSO_5)_2$, $ZnSO_5$. Presently preferred are ammonium and alkali metal peroxomonosulfates, most preferably $KHSO_5$. $KHSO_5$ is marketed under the trademark Oxone ® by E. I. DuPont de Nemours and Company, Willmington, Del. Oxone ® is a complex salt of the approximate formula $2KHSO_5 \cdot KHSO_4 \cdot K_2SO_4$.

Non-limiting examples of peroxodisulfates are $LiHS_2O_8$, $Li_2S_2O_8$, $NaHS_2O_8$, $Na_2S_2O_8$, $KHS_2O_8$, $K_2S_2O_8$, $NH_4HS_2O_8$, $(NH_4)_2S_2O_8$, $NH_4KS_2O_8$, $MgHS_2O_8$, $MgS_2O_8$, $CaHS_2O_8$, $Ca_2S_2O_8$, $Zn_2S_2O_8$. $(NH_4)_2S_2O_8$ and $K_2S_2O_8$ are the most readily available peroxodisulfates. Presently the peroxidisulfoates are not the preferred oxidants in the process of this invention.

Non-limiting examples of acids having a pKa value of less than 4 are $H_2SO_4$, $KHSO_4$, $NaHSO_4$, $H_2SO_5$, $H_2S_2O_8$, HCl, $HClO_3$, $HClO_4$, $HNO_3$, $H_3PO_4$, oxalic acid, trichloroacetic acid. Presently preferred is $H_2SO_4$, which is generally added in form of a dilute aqueous solution to the sulfolene compound.

When a peroxomonosulfate or peroxodisulfate and an acid are added to a sulfolene, said peroxosulfate compound and acid can be charged to the sulfolene compound in any order, either sequentially or essentially simultaneously. It is presently preferred to add the acid first and then the peroxosulfate compound, preferably an alkali metal peroxomonosulfate, most preferably $KHSO_5$. The mixing of the sulfolene, the acid, and the peroxodi- or peroxomonosulfate can be carried out in any vessel. Some agitation is generally preferred so as to afford intimate contact of these three ingredients and to facilitate the removal of gaseous $SO_2$ from the liquid mixture. This process can be carried out batchwise or continuously. Also a suitable solvent such a water can be present.

In a preferred embodiment, the acid is added first to a sulfolene, preferably in such an amount as to attain a pH of the sulfolene ranging from about 1 to 4. Then a gas such as oxygen, nitrogen, air, helium, argon and the like is introduced near the bottom of the vessel containing the sulfolene compound and bubbled through the sulfolene compound, so as to sweep out a portion of dissolved sulfur dioxide. Thereafter, the peroxosulfate compound is added. The flow rate of the introduced gas greatly depends on the amount of sulfolene to be purified, the concentration of $SO_2$ in sulfolene, the desired rate of $SO_2$ removal, and the configuration of reactor and gas inlet means. Generally the above described purging with a gas is carried out for a time period ranging from about 1 minute to about 1 hour.

The temperature during the intimate contact of the sulfolene compound and the peroxosulfate compound, preferably a peroxomonosulfate plus an acid having a pKa of less than 4, is not believed to be critical. Generally, the temperature during said contacting ranges from about 10° C. to about 80° C., preferably from about 20° C. to about 50° C. The pressure during the contacting of the sulfolene compound and peroxosulfur compound can be atmospheric, subatmospheric (i.e., under vacuum conditions) and superatmospheric (i.e., above 1 atm). Generally the pressure is atmospheric (i.e., approximately 1 atm or 15 psia). The ratio of the amount of peroxosulfate compound (e.g., $KHSO_5$) to the amount of sulfolene in the process of this invention generally ranges from about 0.1:1 to about 20:1, preferably about 0.5:1 to about 5:1, millimoles of $HSO_5^-$ or $SO_5^{-2}$ (e.g., $KHSO_5$) per 100 g sulfolene. The pH of the sulfolene compound generally ranges from about 1 to about 4 (after addition of the acid).

The sulfolene compound, preferably 3-sulfolene, which has been purified by the above described treatment with a peroxosulfate compound, preferably an alkali metal peroxomonosulfate and an acid having a pKa of less than 4, can thereafter be catalytically hydrogenated to a sulfolane compound. Processes for hydrogenating sulfolenes, e.g., in the presence of a nickel containing hydrogenation catalyst such as Raney nickel, and for recovering sulfolanes from the reaction mixture have been described in U.S. Pat. Nos. 3,152,144; 3,417,103; 3,514,469; 3,622,598 and 4,188,327, herein incorporated by reference. Presently preferred hydrogenation conditions include a Raney catalyst, an initial hydrogen pressure of about 500–2000 psig, a reaction temperature of about 100°–150° C., and a reaction time ranging from about 10 minutes to about 2 hours. The previously added oxidizing agent of this invention, ingredients, e.g, a peroxosulfate compound and an acid is generally not separated from the sulfolene compound prior to the hydrogenation and is thus present during the catalytic hydrogenation reaction.

The following examples are presented to further illustrate this invention without unduly limiting the scope of this invention.

EXAMPLE I

This example illustrates the use of hydrogen peroxide for the purification and subsequent catalytic hydrogenation of 3-sulfolene, substantially in accordance with U.S. Pat. No. 3,152,144. The hydrogenation catalyst was a commercial Raney nickel catalyst, obtained from Strem Chemicals, Inc., Newburyport, MA and was identified as a fine Raney nickel, catalog number 28-1890. The catalyst material used in the experiments of Examples I and II was a settled mixture of this Raney nickel catalyst and about 20–30 weight-% water. 3-Sulfolene was manufactured by Phillips Chemical Company, Bartlesville, Okla.; and hydrogen peroxide was employed as a 10 weight-% aqueous solution. A 300 mL autoclave equipped with stirrer, pressure gauge and thermocouple was used for the catalytic hydrogenation tests. The decrease in pressure during the reaction was considered a measure of the rate of hydrogen consumption and thus a measure of the rate of the hydrogenation.

The reaction temperature of the hydrogenation in all runs ranged from about 110° to 120° F. In several runs, dilute sulfuric acid was added to sulfolene before the hydrogenation so as to lower the pH of sulfolene. In addition, in the same runs the acidified sulfolene was purged by passing flowing air through sulfolene at room temperature for about 30 minutes so as to sweep out dissolved $SO_2$, which retards the subsequent catalytic hydrogenation. Pertinent test conditions and results of these control runs are summarized in Table I.

TABLE I

| Run | Wt. of Sulfolane (g) | Wt. of Catalyst[1] (g) | pH of Sulfolene | Air-Purged | Millimoles of Added $H_2O_2$ | Reaction Temp (°F.) | Pressure (Psig) Initial | Pressure (Psig) Final | Reaction Time (min.) | Psig Drop per Minute per 100 g Sulfolene |
|---|---|---|---|---|---|---|---|---|---|---|
| 1 | 115 | 1.45 | — | No | 2.9 | 107–119 | 1000 | 225 | 105 | 6.4 |
| 2 | 122 | 1.45 | — | No | 1.5 | 108–116 | 1000 | 215 | 80 | 8.0 |
| 3 | 126 | 1.45 | 1.6 | Yes | 0.9 | 110–121 | 1000 | 240 | 85 | 7.1 |
| 4 | 121 | 1.45 | 1.6 | Yes | 0.6 | 112–118 | 1000 | 190 | 90 | 7.4 |
| 5 | 120 | 1.45 | 1.6 | Yes | 0.3 | 111–117 | 1000 | 240 | 95 | 7.5 |

[1]A settled mixture of Raney nickel and about 20–30 weight % $H_2O$.

Data in Table I show that the average rate of the hydrogen pressure drop (a measure of the rate of sulfolene hydrogenation) in control runs 1–5 was about 7.3 psig per minute per 100 g sulfolene, at a temperature of about 110°–120° F., in the presence of 1.45 grams of wet Raney nickel. Air purging did not have a significant effect on the hydrogenation rate.

EXAMPLE II

This example illustrates the use of an acidified monoperoxosulfate solution for the purification and subsequent catalytic hydrogenation of sulfolane. The experimental procedure was essentially the same as the one described in Example I, with the exception that Oxone ® (marketed by Du Pont de Nemours & Company; Wilmington, Del.), a monoperoxosulfate of the formula $2KHSO_5 \cdot KHSO_4 \cdot K_2SO_4$ (molecular weight: 614), was used in lieu of $H_2O_2$. Pertinent test conditions and results of invention runs are summarized in Table II.

TABLE II

| Run | Wt. of Sulfolane (g) | Wt. of Catalyst[1] (g) | pH of Sulfolene | Air-Purged | Millimoles of Added $HSO_5^-$ | Reaction Temp (°F.) | Pressure (Psig) Initial | Pressure (Psig) Final | Reaction Time (min.) | Psig Drop per Minute per 100 g Sulfolene |
|---|---|---|---|---|---|---|---|---|---|---|
| 6  | 117 | 1.42 | —   | No  | 1.6 | 110–116 | 1000 | 100 | 49 | 15.7 |
| 7  | 80  | 1.42 | —   | No  | 1.3 | 114     | 1000 | 148 | 80 | 13.3 |
| 8  | 110 | 1.45 | 2.0 | No  | 1.6 | 110–118 | 1000 | 165 | 60 | 12.7 |
| 9  | 70  | 1.45 | 3.0 | No  | 1.0 | 111–113 | 1000 | 830[1] | 60 | 5.7[2] |
| 10 | 127 | 1.45 | 2.5 | Yes | 2.0 | 115–119 | 1000 | 125 | 25 | 27.8 |
| 11 | 127 | 1.45 | 2.5 | Yes | 1.6 | 113–119 | 1000 | 125 | 25 | 27.6 |
| 12 | 126 | 1.45 | 2.0 | Yes | 1.3 | 114–124 | 1000 | 185 | 44 | 14.7 |
| 13 | 124 | 1.45 | 3.0 | Yes | 1.0 | 113–116 | 1000 | 150 | 57 | 12.0 |

[1]A settled mixture of Raney nickel and about 20–30 weight % $H_2O$.
[2]Believed to be erroneous.

A comparison of the data in Tables II and I shows that the hydrogen pressure drop per minute per 100 grams of sulfolene was significantly higher when Oxone ® peroxymonosulfate was employed in lieu of $H_2O_2$. The average pressure drop rate per 100 gram of sulfolene of invention runs 6–13 employing 1.0–2.0 millimoles of $SO_5^-$ (Table II) was 16.2, compared with 7.3 of control runs 1–5 employing 0.3–2.9 millimoles of $H_2O_2$ (Table I). One mole of both $H_2O_2$ and $HSO_5^-$ can donate one gram-atom (i.e., 2 gram equivalent) of oxygen in oxidation reactions.

Therefore, unexpectedly the rate of hydrogen consumption, and thus the rate of hydrogenation of sulfolene, in the presence of acidified peroxomonosulfate was more than twice the rate of hydrogenation in the presence of of an equivalent amount of hydrogen peroxide. In addition, air purging generally had a beneficial effect on the rate of reaction when acidified peroxomonosulfate was employed, whereas air purging did not exhibit such a beneficial effect when $H_2O_2$ was used (see Table I).

Reasonable variations and modifications can be made in this invention without departing from the limit and scope thereof.

I claim:

1. A process for purifying a sulfolene compound comprising the step of contacting said sulfolene compound, which contains dissolved $SO_2$, with at least one oxidizing agent selected from the group consisting of (a) peroxomonosulfuric acid, (b) peroxodisulfuric acid, (c) peroxomonosulfates and at least one acid having a pKa of less than 4, and (d) peroxodisulfates and at least one acid having a pKa of less than 4, under such conditions as to produce a sulfolene compound having a reduced level of dissolved $SO_2$; wherein said acid in (c) and (d) can be (a) or (b).

2. A process in accordance with claim 1, wherein the sulfolene compound is 3-sulfolene.

3. A process in accordance with claim 2, wherein said oxidizing agent is at least one of ammonium and alkali peroxomonosulfates plus said acid having a pKa of less than 4.

4. A process in accordance with claim 2, wherein the oxidizing agent consists essentially of $KHSO_5$ and $H_2SO_4$.

5. A process in accordance with claim 4, wherein the concentration of $KHSO_5^-$ in 3-sulfolene ranges from about 0.1:1 to about 20:1 millimoles of $KHSO_5$ per 100 grams of 3-sulfolene, and the pH of the 3-sulfolene (after addition of said acid) ranges from about 1 to about 4.

6. A process in accordance with claim 5, wherein said concentration of $KHSO_5$ in 3-sulfolene ranges from about 0.5:1 to about 5:1 millimoles of $KHSO_5$ per 100 grams of 3-sulfolene.

7. A process in accordance with claim 6, wherein said contacting is carried out at a temperature ranging from about 10° C. to about 80° C.

8. A process for purifying a sulfolene compound comprising the steps of
   (A) adding an acid having a pKa of less than 4 to a sulfolene compound which contains dissolved $SO_2$,
   (B) passing a stream of gas through the thus acidified sulfolene compound so as to remove a portion of said dissolved $SO_2$,
   (C) treating the sulfolene compound treated by step (B) with at least one oxidizing agent selected from the group selected from the group consisting of (a) peroxomonosulfuric acid, (b) peroxodisulfuric acid, (c) peroxomonosulfates and at least one acid having a pKa of less than 4, and (d) peroxodisulfates and at least one acid having a pKa of less than 4, under such conditions as to remove a further portion of dissolved $SO_2$ from said sulfolene compound, and to produce a sulfolene compound having a reduced level of dissolved $SO_2$; wherein said acid in (c) and (d) can be (a) or (b).

9. A process in accordance with claim 8, wherein said oxidizing agent is at least one of ammonium and alkali peroxomonosulfates plus said acid having a pKa of less than 4.

10. A process in accordance with claim 8 wherein the sulfolene compound is 3-sulfolene, said acid is $H_2SO_4$ and said peroxosulfate compound is $KHSO_5$.

11. A process in accordance with claim 10, wherein the pH of 3-sulfolene after addition of $H_2SO_4$ in step (B) ranges from about 1 to about 4.

12. A process in accordance with claim 11, wherein the ratio of millimoles of $KHSO_5$ to 100 grams of 3-sulfolene ranges from about 0.5:1 to about 5:1.

13. A process in accordance with claim 8, wherein the temperature in both steps (A) and (B) ranges from about 10° C. to about 80° C.

14. A process for hydrogenating a sulfolene compound to a sulfolane compound comprising the steps of:
   (A) contacting said sulfolene compound, which contains dissolved $SO_2$, with at least one oxidizing agent selected from the group consisting of (a) peroxomonosulfuric acid, (b) peroxodisulfuric acid, (c) peroxomonosulfates and an acid having a pKa of less than 4, and (d) peroxodisulfates and an acid having a pKa of less than 4, under such conditions as to produce a sulfolene compound having a reduced level of dissolved $SO_2$; wherein the acid in (c) and (d) can be (a) or (b);
   (B) contacting said sulfolene compound having a reduced level of $SO_2$ with hydrogen and a hydrogenation catalyst under such hydrogenation conditions as to produce a sulfolane compound.

15. A process in accordance with claim 14, wherein the sulfolene compound is 3-sulfolene, and said catalyst is a nickel containing catalyst.

16. A process in accordance with claim 15, wherein the oxidizing agent is at least one of ammonium and alkali metal peroxomonosulfates plus an acid having a pKa of less than 4.

17. A process in accordance with claim 15 wherein said oxidizing agent is $KHSO_5$, said acid is $H_2SO_4$, and said catalyst is Raney nickel.

18. A process in accordance with claim 17 wherein the ratio of millimoles of $KHSO_5$ to 100 grams of 3-sulfolene ranges from about 0.1:1 to about 20:1, and the pH of 3-sulfolene after addition of $H_2SO_4$ ranges from about 1 to about 4.

19. A process in accordance with claim 18, wherein the hydrogenation reaction (B) is carried out at an initial hydrogen pressure of about 500–2000 psig, a reaction temperature of about 100°–150° C., and a reaction time ranging from about 10 minutes to about 2 hours.

* * * * *